United States Patent [19]

Chang et al.

[11] Patent Number: 5,401,506
[45] Date of Patent: Mar. 28, 1995

[54] STABILIZED INSECT NEMATODE COMPOSITIONS

[75] Inventors: Frank N. Chang, Dresher; Michael J. Gehret, Lebanon, both of Pa.

[73] Assignee: Temple University, Pa.

[21] Appl. No.: 930,484

[22] Filed: Aug. 14, 1992

Related U.S. Application Data

[63] Continuation-in-part of Ser. No. 624,134, Dec. 7, 1990, abandoned.

[51] Int. Cl.⁶ .................. A01N 25/28; A01N 63/00
[52] U.S. Cl. .................................. 424/408; 424/410; 424/418; 424/419; 424/420; 424/488; 424/498; 424/499
[58] Field of Search ............... 424/493, 484, 485, 486, 424/487, 488, 408, 405, 410

[56] References Cited

U.S. PATENT DOCUMENTS

| | | | |
|---|---|---|---|
| 3,113,066 | 12/1963 | Emond . | |
| 3,271,243 | 9/1966 | Cards et al. | 167/22 |
| 3,666,557 | 5/1972 | Jensen et al. | 127/32 |
| 3,791,983 | 2/1974 | Maierson . | |
| 4,178,366 | 12/1979 | Bedding | 424/93 |
| 4,187,290 | 2/1980 | Goldberg . | |
| 4,215,115 | 7/1980 | DiSanzo | 424/216 |
| 4,424,214 | 1/1984 | Okada et al. | 424/200 |
| 4,615,883 | 10/1986 | Nelsen et al. | 424/84 |
| 4,640,929 | 2/1987 | Mitsudera et al. | 514/436 |
| 4,657,582 | 4/1987 | Huber | 424/410 X |
| 4,666,939 | 5/1987 | Voege et al. | 514/482 |
| 4,701,326 | 10/1987 | Nelsen et al. | 424/410 X |
| 4,753,799 | 6/1988 | Nelsen et al. | 424/408 |
| 4,765,225 | 8/1988 | Yukawa et al. | 119/15 |
| 4,859,377 | 8/1989 | Shasha et al. | 424/410 X |
| 4,900,753 | 2/1990 | Sutherland et al. | 514/450 |
| 4,910,219 | 3/1990 | Sutherland et al. | 514/450 |
| 4,911,952 | 3/1990 | Doane et al. | 424/410 X |
| 5,141,744 | 8/1992 | Chang et al. | 424/93 |

FOREIGN PATENT DOCUMENTS

| | | |
|---|---|---|
| 0180743 | 9/1985 | European Pat. Off. . |
| 0180743 | 5/1986 | European Pat. Off. . |
| 92902263 | 2/1994 | European Pat. Off. . |
| 8900601 | 1/1989 | WIPO . |
| 9101736 | 2/1991 | WIPO . |

OTHER PUBLICATIONS

*Nematodes for Biological Control of Insects*, Poinar, CRC Press, Inc, Boca Raton, Fla. 1979. (not provided herewith).

*Environmental Entomology*, 17, Dunkle & Shasha, pp. 120–126, 1988.

Chemical Abstracts, vol. 112, No. 21, 21 May 1990, Columbus, Ohio, U.S.; abstract No. 193820e, E. Grosse "Agent for terminating drying-induced diapause in the nematode *Heterodera avenae*", pp. 268 & DD-A-272 988 (E. Grosse et al.) 1 Nov. 1989.

Journal of Economic Entomology, vol. 79, No. 3, Jun. 1986, College Park, Maryland US, pp. 668–671, T. L. Ladd, Jr. "Influence of sugars on the feeding response of Japanese beetles (*Coleoptera: Scarabeidae*)".

*Primary Examiner*—Thurman K. Page
*Assistant Examiner*—Neil Levy
*Attorney, Agent, or Firm*—Ratner & Prestia

[57] ABSTRACT

An insecticidal composition comprising a first composition having an effective amount of at least one species of entomopathogen distributed in a matrix. A second composition selected from vegetable oil, crop oil and partially hydrogenated oil containing mono- and di-glycerides surrounds the first composition and significantly prolongs nematode viability. The matrix is a nematode-containing macrogel or paste of partially hydrogenated oils containing mono- and di-glycerides. The macrogel matrix is selected from a continuous polymer macrogel or microcapsule-containing macrogel. Partially hydrogenated oils containing mono- and di-glycerides, (e.g., Crisco ® shortening), can also be mixed with free nematodes to produce a paste formulation. Trapping nematodes in a Crisco ® matrix formulation along with a water retentive polymer results in increased protection against desiccation and significantly prolongs viability during storage. An insect feeding stimulant, such as raffinose, may also be added to the mix.

30 Claims, No Drawings

STABILIZED INSECT NEMATODE COMPOSITIONS

This application is a continuation-in-part of application Ser. No. 07/624,134, filed Dec. 7, 1990, now abandoned.

BACKGROUND OF THE INVENTION

1. Field of the Invention

This invention relates generally to insecticidal compositions containing nematodes which are useful for the biological control of noxious insects.

2. Description of Related Art

Insect nematodes (Steinernematidae, Heterorhabditidae, Mermithidae) have been shown to be highly effective bioinsecticides (Poinar, "Nematodes for Biological Control of Insects" CRC Press, Inc., Boca Raton, Fla., 1979). However, insect nematodes require moist conditions to survive and function. When nematodes are dried they lose activity rapidly; subsequent rehydration fails to restore the lost activity. One method of preserving nematodes in a moist environment is via the microencapsulation processes of U.S. Pat. Nos. 4,615,883, 4,701,326, and 4,753,799. This art microencapsulates the nematodes in calcium alginate. The alginate microcapsules, however, have several drawbacks. They are fairly large and rigid and consequently are not appealing to insects as well as being out of the chewing range of smaller insects. Additionally, the ability of the alginate microcapsules to maintain moisture conditions conducive to survival of the nematodes has also been questioned (Dunkle and Shasha, Environ. Entomol., Vol. 17,120–126, 1988). To reduce the rate of desiccation, others have used water thickeners, mineral oil, or surfactants. See, for example, U.S. Pat. No. 4,178,366. With insect nematodes most of these approaches are ineffective in preserving the moisture content and consequently the biological activity. Some have adverse effects on biological activity or repel the target insects, thereby making them ineffective for their intended purpose.

Another factor greatly limiting the effective use of nematodes for biological control of insects is the inability of the nematodes to survive for an extended period of time at high temperatures. High temperatures are frequently encountered in the field during summer months and in unregulated storage warehouses.

U.S. Pat. No. 3,271,243 (Cords et al.) discloses an oil-water suspension of *Bacillus thuringiensis*, including vegetable, animal or mineral oils, such as corn oil. The resulting insecticide is dependent on pH and salt concentration.

U.S. Pat. No. 4,859,377 (Shasha et al.) discloses the encapsulation of corn oil and entomopathogens in starch. Encapsulation of *Bacillus thuringiensis* and of nuclear polyhedrosis virus is demonstrated in the presence of corn oil.

U.S. Pat. No. 4,178,366 (Bedding) discloses an oil suspension of nematodes. The harvested, unprotected nematodes are stored in oil and/or wax. The patent also indicates that nematodes may be kept alive when suspended in water through which air is bubbled at a rate sufficient to insure that the nematodes are subject to some degree of agitation.

U.S. Pat. No. 4,765,275 (Yukawa et al.) discloses an improved method for the storage and transport of nematodes. This patent recommends the storage of nematodes under substantially anaerobic conditions as a means for prolonging their viability.

It is an object of this invention to provide a formulation for keeping nematodes viable.

Another object of this invention to provide stable nematode formulations that can be stored at high temperatures without appreciable loss of activity. Preferably the nematode formulation should be stable for months at 32° C. or for several weeks at 37° C.

Another object of the invention is to provide a means to maintain the nematodes in a moist environment. Preferably, the nematodes may be maintained in a moist environment for an extended period of time even at high temperatures.

Still a further object is to provide means to attract insects to the formulations and, once attracted, to induce the insects to consume the moist and viable nematodes.

SUMMARY OF THE INVENTION

This invention is drawn to an insecticidal composition comprising a first composition having an effective amount of at least one species of entomopathogen distributed in a matrix, surrounded by a second composition selected from vegetable oil, crop oil and partially hydrogenated oil containing mono- and di-glycerides.

The matrix is a nematode-containing macrogel or paste of partially hydrogenated oil containing mono- and di-glycerides. The macrogel matrix is selected from a continuous polymer macrogel or microcapsule-containing macrogel.

The addition of nematode macrogels or capsules to vegetable or crop oil such as corn oil, soybean oil, palm oil and cottonseed oil; or partially hydrogenated oil containing mono- and di-glycerides significantly prolong nematode viability during storage.

When partially hydrogenated oils containing mono- and di-glycerides (e.g., Crisco ® shortening) are mixed with free nematodes, a paste formulation results. Trapping nematodes in a Crisco ® paste formulation along with a water retentive polymer results in increased protection against desiccation and significantly prolongs viability during storage. A water retentive compound, such as a water retentive polymer, is required for maintaining the nematodes viable for a long period of time in an open environment; however, a water retentive compound is not required for short time periods in an open environment or for uses in environments where water evaporation is not likely, such as in a sealed environment.

According to an alternative embodiment of the invention, 0.01 to 1.0% hydrogen peroxide is included in the nematode matrix or paste formulations. The inclusion of from 0.01 to 1.0% hydrogen peroxide generates oxygen which is trapped and made available to prolong the life of the nematodes. Alternatively, nematodes may be encapsulated in the presence of hydrogen peroxide. The nematodes are entrapped inside a polymer made of either gellan gum, carrageenan or calcium alginate, together with the trapped oxygen.

When stored in vegetable oil, crop oil or partially hydrogenated oil containing mono- and di-glycerides, such nematode continuous matrices or microcapsules are stable at high temperatures for many months.

According to another alternative embodiment of the invention, an insect feeding stimulant, such as raffinose, is included in the nematode matrix in paste formulations.

DETAILED DESCRIPTION OF THE INVENTION

The problem with desiccation and inactivation of entomopathogens such as insect nematodes, bacteria, baculoviruses or fungal pathogens can be substantially ameliorated by this invention. While Bedding uses high concentrations of paraffin wax and paraffinic oil to retard evaporation of insect nematodes, such a formulation, however, is not appealing to insects. We have unexpectedly found that partially hydrogenated vegetable oil or crop oil containing mono- and di-glycerides, such as Crisco ® shortening, not only are conducive to nematodes as insecticides, but also significantly prolong the viability of nematodes during storage. The presence of additional vegetable oil or crop oil in the formulations renders them highly attractive to certain insects. Thus the insects are attracted to the baits containing the nematodes. In addition, vegetable oil and crop oil, including partially hydrogenated oils, also have a beneficial effect in preserving the viability of nematodes. Thus, a formulation including a nematode distributed in a matrix and surrounded by vegetable oil, crop oil or a partially hydrogenated oil containing mono and di-glycerides is a useful formulation for storing nematodes and keeping them viable to attract and control insects.

The active ingredient in one embodiment of this invention comprises the entomopathogens distributed within the matrix. Such matrices include a macrogel matrix, wherein nematodes are distributed continuously throughout a polymer matrix or encapsulated in a polymer matrix; and a Crisco ® paste matrix which entraps nematodes. Thus, the macrogel matrix may be a continuous polymer macrogel or a microcapsule-containing macrogel. The problem of desiccation of the entomopathogens is substantially ameliorated by the addition of vegetable oil, crop oil or partially hydrogenated oil containing mono- and di-glycerides during storage.

The entomopathogens which are distributed and immobilized in a continuous insect-consumable matrix, one of the matrices of the present invention, along with a source of water for the entomopathogens, have significantly enhanced viability. The final product may be a continuous matrix in which the nematodes, or the like, are embedded, together with a source of moisture, and, optionally, other additives, such as our newly discovered insect feeding stimulant (raffinose) or other insect attractants or such stabilizers as may be required by the contemplated use of the insect bait device.

The continuous macrogel matrix, an insect-consumable macrogel, is produced by methods whereby, the entomopathogens are suspended in an aqueous solution of a gel-forming matrix in the presence of an inert water retaining compound. Gelation is then induced by whatever means are appropriate for the selected matrix. The resultant insecticidal continuous matrix then contains a distribution of entomopathogens and water reservoirs. The matrix may be stored for an indefinite period without adverse effects on the viability of the entomopathogens and may be cut into smaller pieces as desired.

The continuous matrix-forming polymer is selected from natural, naturally derived, and synthetic polymers, with the provisos that the matrix per se and the gelation conditions are neither harmful to the entomopathogens nor interfere with the effectiveness of the pathogens. Suitable matrix-forming polymers include, but are not limited to, agarose, carbopols, carrageenan, dextran, guar gum, and other heteropolysaccharides, such as gellan gum. One advantage associated with the use of the natural polysaccharides is that these are often attractive as food for the insects whose demise is desired.

A preferred source of the matrix-forming polymer is the cationically gellable heteropolysaccharides, such as those disclosed in U.S. Pat. No. 4,326,052 and U.S. Pat. No. 4,326,053, the disclosures of which are incorporated by reference herein. A suitable variety of this material is available commercially as Gel-Gro ® gellan gum from ICN Biochemicals, Cleveland, Ohio.

The gelation time of the Gel-Gro ® gellan gum is easily controlled by varying the polymer concentration, the concentration and type of gelling agent, and the temperature. Preferably, the Gel-Gro ® liquid polymer concentration is between 0.2% and 5.0% by weight, the gelling agent is a cation, and the concentration of gelling agent is from 0.1 mM to 500 mM. Most preferably, the polymer concentration is from about 0.6% to 1.2% by weight, the gelling agent is a divalent cation, and the cation concentration is from about 0.5 mM to 25.0 mM. The most preferable conditions result in gelation times of about 1 to 15 minutes. When spraying formulations are desired, a cation concentration in excess of 25 mM is preferred to obtain rapid gelation.

Suitable divalent cations include barium, calcium, copper(II), iron(II), magnesium, manganese, and zinc(II). Monovalent cations such as ammonium, cesium, lithium, potassium, and sodium, may also be used to induce gelation, albeit at higher concentrations. Trivalent ions such as aluminum and iron(III) are also useful.

In another embodiment of the invention, Crisco ® is used in the process of producing a nematode-containing paste matrix such that Crisco ® takes the place of the matrix-forming polymer. Accordingly, ions are unnecessary for the formation of the Crisco ® matrix.

The hydrated, water retentive compound which may be incorporated into the matrices, polymer and Crisco ®, as the water reservoir for the entomopathogen is typically a water-absorbing polymer, such as a hydrophilic acrylic, acrylamide, polyurethane or starch-based polymer. Such polymers, commonly known as hydrogels, will absorb and retain several hundred times their weight in water and will slowly release the absorbed water. Representative examples of these materials are California Crystals ®, a water-absorbing acrylic polymer available from J & G Agrow-tek, Rancho Cordova, Calif. and Water Grabber ®, a water-absorbing acrylamide from FP Products, Inc., Atlanta, Ga. Other materials which exhibit similar affinities for water may be substituted. If included, the amount of hydrated, water retentive polymer present in the matrix is generally about 25% to about 75%, although the choice and concentration of pathogen and the envisioned environment may lead to significant departures from these norms.

The formulation may be used without a water retentive polymer if the intended use permits this approach. For example, the water retentive polymer is not needed if the nematodes only need to remain viable for a relatively short time, or if water evaporation is not a concern, such as in a sealed environment. In general, the water evaporation rate of a formulation without a water retentive polymer is three times faster than the water evaporation rate of a formulation with a water retentive polymer.

This invention may also be used in the process of microencapsulating nematodes as well as in the storage thereof. $H_2O_2$ may be incorporated into microencapsulation techniques as well. Furthermore, microencapsulated nematodes may be stored in vegetable oil or crop oil, such as corn oil, soybean oil, palm oil, cottonseed oil and the like; or partially hydrogenated oil containing mono- and di-glycerides. Accordingly, any vegetable oil or crop oil that is compatible with nematode capsules, such as capsules prepared with gellan gum, carrageenan and calcium alginate may be used.

As previously noted, the entomopathogen is selected from among those pathogens which control noxious insect infestations. Baculoviruses, such as nuclear polyhedrosis virus; bacteria, such as *Bacillus thuringiensis;* fungal pathogens, such as *Beauveria bassiana, Metarhizium anisopliae,* and *Nomuraea rileyi;* and nematodes, such as *Steinernema carpocapsae,* (also known as *Steinernema feltiae* and *Neoaplectana carpocapsae*) and *Heterorhabditis bacteriophora* (also known as *Heterorhabditis heliothidis*) are among the more useful pathogens. Selection of the entomopathogens is not limited to those described herein, but is well within the purview of one skilled in the art of natural predation. Nematodes are particularly well-suited for the practice of this invention. However, the only limitations on the pathogens are that they not be inactivated by the conditions of gelation or the composition of the matrix or microcapsule. Since the nematodes will reproduce in the insect host, only a few need be incorporated in a discrete sample to provide control. Of course, millions of pathogens may be easily incorporated. In the practice of this invention, we have found that nematode concentrations from a few up to about 500,000 per milliliter are most useful. For other pathogens, such as *Bacillus thuringiensis,* the macrogel may contain as much as 20% by weight.

According to an alternative embodiment of the invention, 0.01 to 1.0% hydrogen peroxide is included in the nematode matrix or paste formulations. The inclusion of from 0.01 to 1.0% hydrogen peroxide generates oxygen which is trapped and made available to prolong the life of the nematodes. The inclusion of hydrogen peroxide is a preferred embodiment for uses of the formulation at high temperatures; however, a formulation of the present invention without hydrogen peroxide is useful for storing and keeping nematodes viable at lower temperatures.

According to another embodiment of the present invention, an attractant or feeding stimulant may be added to the nematode matrix or paste formulations. The particular insect feeding stimulant selected depends upon the target insect sought to be controlled. For example, if corn rootworms are sought to be controlled, a feeding stimulant which attracts corn rootworms may be added to the formulation. It has been discovered that raffinose is effective to attract corn rootworms.

The present invention is more clearly demonstrated by the following examples.

EXAMPLE 1

Four nematode paste formulations were prepared. Formulation 1 was a control and contained no nematodes whereas Formulations 2 to 4 contained approximately 200,000 nematodes (*Steinernema carpocapsae* strain All) in 5 ml of water. Five ml of a crushed, fully swelled and expanded water retentive polymer were added to each of the above solutions which were then dispersed thoroughly by mixing slowly into 10 ml of partially hydrogenated oil containing mono- and di-glycerides (e.g. Crisco ®shortening). Formulation 2 was considered to be the basic paste formulation, i.e., a formulation including the nematodes, water, the water retentive polymer and the above-mentioned partially hydrogenated oil. Formulation 3 contained the basic paste formulation plus a corn rootworm feeding stimulant (raffinose) at a final concentration of 0.25%. Formulation 4 contained in addition to the basic paste formulation and the raffinose (0.25%), corn oil as a rootworm attractant (Mazola ®at a final concentration of 10%). 0.8 ml of each of above formulations were placed into a plastic tube and placed into soil in a 500 ml plastic beaker. Each beaker contained 10 corn rootworms (*Diabrotica spp.*) and a ten-day old corn plant.

Table 1 shows various data for each of the four formulations. Table 1 shows the number of rootworms dead after seven days and the corresponding control rate for each formulation. Table 1 also shows the number of nematodes present in each dead corn rootworm and shows plant height for each formulation.

TABLE 1

|  | Formulation | | | |
|---|---|---|---|---|
|  | 1 | 2 | 3 | 4 |
| Corn Rootworm | | | | |
| Dead/Total | 0/10 | 9/10 | 10/10 | 10/10 |
| % control | 0% | 90% | 100% | 100% |
| No. of nematodes present in each dead corn rootworm | 0 | >100 | >100 | >100 |
| Plant height | | | | |
| Beginning of expt. | 5" | 5" | 5" | 5" |
| End of Expt. | 5" | 10" | 12" | 12" |
| Increase in plant height | 0" | 5" | 7" | 7" |

Table 1 shows that after seven days, nine out of ten corn rootworm were dead in the soil containing the basic paste formulation (Formulation 2). The sole surviving corn rootworm was not found to be feeding on roots. In contrast, all corn rootworms were still alive and actively feeding on the corn plant treated by Formulation 1 (control). Thus, the basic nematode paste formulation is effective against corn rootworms. The addition of a specific corn rootworm feeding stimulant (raffinose) apparently speeded up the consumption of nematodes by rootworms (Formulation 3). Formulation 4 containing raffinose and a corn rootworm attractant (Mazola ®corn oil) also was effective against corn rootworms.

Table 1 also shows the corn plant height treated with the four formulations above. The plant height at the beginning of experiment was 5" and no additional increase in height was observed with Formulation 1 after 7 days. The corn plant treated with Formulation 2, on the other hand, had attained a plant height of 10" after 7 days. Slightly higher plant heights (12") were found for both Formulations 3 and 4, again reflecting the faster infection of rootworms due to the presence of the feeding stimulant (raffinose). Subsequent dissection of dead rootworms in Formulations 2, 3, and 4 showed that each dead rootworm contained over 100 nematodes.

From these results, one can conclude that the basic nematode paste formulation without a feeding stimulant (raffinose) is effective against corn rootworms. The addition of raffinose either alone or together with a corn rootworm attractant (corn oil) are preferred embodiments of the invention and result in a faster infection of corn rootworms and a larger increase in plant height.

A nematode paste formulation without a water retentive polymer was also prepared. Although it was found to have similar infectivity initially, its stability in soil is reduced because the water in this experiment was subject to evaporation. Thus, formulations containing a water retentive compound, such as a water retentive polymer, are preferred.

EXAMPLE 2

Stability of nematodes at high temperatures

Until now, nematodes could only be stored at low temperatures (e.g. 16° C. or lower) with a short shelf life. When stored at 32° C., nematodes are inactivated quickly, usually within one day. We unexpectedly discovered that the addition of hydrogen peroxide allows nematodes to be stored at 32° C. for many months. Stable nematode preparations can be prepared as follows: approximately 20,000 nematodes (*Steinernema carpocapsae* strain All) in 0.5 ml deionized water were mixed with cool 2.5 ml of a 1% gellan gum (e.g. Gel-Gro ®) solution containing 0.1% hydrogen peroxide (final concentration). The Gel-Gro ® solution was prepared by dissolving 0.1 g in 10 ml deionized water followed by either heating in a waterbath or autoclaving for 3 minutes.

A solution of 0.2M calcium chloride containing 0.1% hydrogen peroxide (final concentration) was then prepared. The above nematode solution was dropped into the calcium chloride solution. To insure that nematodes are concentrated at the center of the finished capsule, the initial stirring speed should be very slow (50 to 80 rpm). After about 3 to 5 minutes at this low speed, the stirring speed was then increased to about 300 to 500 rpm and maintained at this speed for an additional 20 minutes. The resultant nematode Gel-Gro ® capsules were then stored in corn oil. The nematode capsules were stable for many months when stored at 32° C. The capsules may also be stored in soybean oil or in partially hydrogenated oil with mono- and di-glycerides (such as Crisco ®). In contrast, when nematode capsules without $H_2O_2$ were stored in oil at 32° C., they only lasted for several days.

Other nematode capsules were also prepared. They include carrageenan and calcium alginate capsules all containing 0.1% hydrogen peroxide. Heterorhabditis instead of Steinernema nematodes were also used and similar results were obtained.

When the nematode capsules originally stored at 32° C. were transferred to 38° C. the nematodes in these capsules survived for more than one week at this high temperature.

EXAMPLE 3

The benefit of $H_2O_2$ on the viability of nematodes in Crisco ® paste formulation during storage at 32° C. is demonstrated in the following experiment. Two paste formulations were made by mixing 0.5 ml of nematodes (*Steinernema carpocapsae* strain All, 40,000 nematodes/ml) with 4.5 ml of Crisco ® shortening. One of the paste formulations contained 0.1% $H_2O_2$ (final concentration) by adding 0.17 ml of 3% $H_2O_2$ whereas the other contained 0.17 ml of water. When the two paste formulations were stored at 32° C., the one without $H_2O_2$ was inactivated in one week, whereas the one containing 0.1% $H_2O_2$ was still active after three weeks.

EXAMPLE 4

Stable nematode preparations were also prepared in the presence of active water reservoir by mixing nematodes with partially hydrogenated vegetable oil together with mono- and di-glycerides (e.g. Crisco ® shortening) and hydrogen peroxide as follows:

5 ml of nematodes (*Steinernema carpocapsae* Strain All, 40,000 nematodes/ml) were mixed for 5 minutes at room temperature with 5 ml of swollen pieces of water retentive polymer (WRP) in the presence of 0.2% hydrogen peroxide and 1% raffinose. The nematode-WRP mixture was then added into 10 ml of Crisco ® shortening. After gentle mixing for 5 minutes, a nematode paste was formed with nematodes evenly distributed in the paste. Such nematode pastes are stable for six to twelve months when stored at 16° C. or lower. When stored at room temperature, they are stable for at least two months.

EXAMPLE 5

Stability of nematode paste formulation in the field

Nematode paste formulation was prepared as described in EXAMPLE 4. Six paraffin section tubes (1.5 ml capacity) were used in this field study. Each tube contained a large piece of previously swollen water retentive polymer gel at the bottom (to provide additional water source) and the remaining tube space was covered with nematode paste (approximately 1.0 ml). The tubes were place three inches below the soil surface on May 14, 1990 in a suburb of Philadelphia. The experiment was stopped on Jun. 19, 1990. The daytime temperature during this period ranged from 75° to 95° F.

| Days | % Nematode Survival |
| --- | --- |
| 0 | 100% |
| 8 | 100% |
| 16 | 100% |
| 23 | 95% |
| 29 | 85% |
| 35 | 80% |

EXAMPLE 6

To show that raffinose is not always required to attract different species of insects, the experimental steps of Example 1 were performed against a totally different insect, a German cockroach. Also, only three formulations were used: (1) a paste formulation without nematodes; (2) a paste formulation with nematodes; (3) a paste formulation with nematodes and raffinose.

TABLE 2

| | 0 days | 2 days | 4 days | 6 days | 8 days |
| --- | --- | --- | --- | --- | --- |
| Formulation 1 (Control) dead/total | 0/10 | 0/10 | 1/10 | 1/10 | 1/10 |
| Formulation 2 (Basic formulation) | 0/10 | 0/10 | 6/10 | 7/10 | 10/10 |
| Formulation 3 Basic formulation plus raffinose | 0/10 | 1/10 | 7/10 | 8/10 | 10/10 |

From the results shown in Table 2, it is evident that the basic nematode paste formulation (Formulation 2) was effective against German cockroaches. Formulation 3 which contains raffinose had only a slight increase in the mortality rate.

While this invention has been disclosed with reference to specific embodiments, it is apparent that other embodiments and equivalent variations of this invention may be devised by those skilled in the art without departing from the true spirit and scope of this invention. The appended claims are intended to be construed to include all such embodiments and equivalent variations.

What is claimed:

1. An insecticidal formulation comprising:
   a first composition selected from the group consisting of:
   a continuous polymer macrogel comprising a heteropolysaccharide, and
   a microcapsule-containing macrogel comprising a heteropolysaccharide,
   having an effective amount of at least one species of entomopathogen distributed therein,
   said first composition surrounded by a second composition comprising a paste of water and hydrogenated oil together with mono- and di-glycerides.

2. A composition of claim 1 wherein said entomopathogen is selected from the group consisting of nematodes, bacteria, baculoviruses, and fungal pathogens.

3. A composition of claim 1 wherein said entomopathogen is selected from the group consisting of *Steinernema carpocapsae* and *Heterorhabditis bacteriophora*.

4. A composition of claim 1 wherein said entomopathogen is nuclear polyhedrosis virus.

5. A composition of claim 1 further including $H_2O_2$ from 0.01% to 1.0% by weight.

6. An insecticidal composition of claim 1 further including an insect feeding stimulant.

7. A formulation comprising a paste of water and hydrogenated oil together with mono- and di-glycerides and containing an effective amount of at least one species of entomopathogen distributed therein.

8. A formulation of claim 7 wherein said paste further includes $H_2O_2$.

9. A formulation comprising a paste and $H_2O_2$, containing an effective amount of at least one species of entomopathogen distributed therein.

10. An insecticidal composition of claim 6 wherein said insect feeding stimulant is raffinose.

11. A composition of claim 1 wherein said heteropolysaccharide is selected from the group consisting of agarose, carbopol, carrageenan, dextran, guar gum and gellan gum.

12. An insecticidal formulation in accordance with claim 1, wherein said hydrogenated oil is an oil selected from oil of vegetables and crops.

13. A formulation in accordance with claim 8 wherein said $H_2O_2$ is from 0.01% to 1.0% by weight.

14. A formulation in accordance with claim 7 further including an insect attractant.

15. A formulation in accordance with claim 9 further including an insect feeding stimulant.

16. A insecticidal formulation in accordance with claim 15 wherein said insect feeding stimulant is raffinose.

17. An insecticidal formulation in accordance with claim 9 further including an insect attractant.

18. A method for controlling insects comprising applying to an area an effective amount of an insecticidal formulation comprising:

a first composition selected from the group consisting of:

a continuous ,polymer macrogel comprising a heteropolysaccharide, and a microcapsule-containing macrogel comprising a heteropolysaccharide, having an effective amount of at least one species of entomopathogen distributed therein, said first composition surrounded by a second composition comprising a paste of water and hydrogenated oil together with mono- and di-glycerides.

19. The method of claim 18 wherein the formulation further comprises $H_2O_2$.

20. The method of claim 19 wherein the insects to be controlled are proximate to the area to which the formulation is applied.

21. The method of claim 19 wherein the formulation is applied to an insect bait device.

22. A method for controlling insects comprising applying to an area an effective amount of an insecticidal formulation comprising a paste of water and hydrogenated oil together with mono- and di-glycerides and containing an effective amount of at least one species of entomopathogen distributed therein.

23. The method of claim 22 wherein the formulation further comprises $H_2O_2$.

24. The method of claim 22 wherein the insects to be controlled are proximate to the area to which the formulation is applied.

25. The method of claim 22 wherein the formulation is applied to an insect bait device.

26. An insecticidal formulation in accordance with claim 1 wherein said at least one species of entomopathogen is selected from entomopathogens which remain active upon mixing with said first composition.

27. A formulation in accordance with claim 8 wherein the $H_2O_2$ is present in an amount of from about 0.01% to 1.0% by weight.

28. A formulation in accordance with claim 9 wherein the $H_2O_2$ is present in an amount of from about 0.01% to 1.0% by weight.

29. A formulation in accordance with claim 1 wherein the mono- and di-glycerides are present in an amount sufficient to render the hydrogenated oil water miscible.

30. A formulation in accordance with claim 12 wherein the mono- and di-glyceride are present in an amount sufficient to render the hydrogenated oil water miscible.

* * * * *

UNITED STATES PATENT AND TRADEMARK OFFICE
CERTIFICATE OF CORRECTION

PATENT NO.   : 5,401,506
DATED        : March 28, 1995
INVENTOR(S)  : Chang et al.

It is certified that error appears in the above-identified patent and that said Letters Patent is hereby corrected as shown below:

On the title page; delete

Item "[73] Assignee: Temple University, Pa."

and insert

--[73] Assignee: Temple University - Of the Commonwealth System of Higher Education, Pa.--.

Signed and Sealed this

Fourteenth Day of May, 1996

Attest:

BRUCE LEHMAN

*Attesting Officer*        *Commissioner of Patents and Trademarks*